(12) United States Patent
Scheele et al.

(10) Patent No.: US 11,426,333 B2
(45) Date of Patent: *Aug. 30, 2022

(54) SOLID HAIR COSMETIC COMPOSITION

(71) Applicant: Henkel AG & Co. KGaA, Duesseldorf (DE)

(72) Inventors: Soeren Scheele, Pinneberg (DE); Manuela Mette, Kleinfeld (DE); Petra Westphal, Neu Wulmstorf (DE); Thomas Schroeder, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/924,586

(22) Filed: Jul. 9, 2020

(65) Prior Publication Data
US 2021/0007943 A1    Jan. 14, 2021

(30) Foreign Application Priority Data

Jul. 10, 2019   (DE) .................. 10 2019 210 155.0

(51) Int. Cl.
| | | |
|---|---|---|
| A61K 8/34 | (2006.01) | |
| A61K 8/36 | (2006.01) | |
| A61K 8/92 | (2006.01) | |
| A61Q 5/12 | (2006.01) | |
| A61K 8/02 | (2006.01) | |
| A61K 8/73 | (2006.01) | |
| A61K 8/362 | (2006.01) | |
| B29C 39/00 | (2006.01) | |
| A61K 8/41 | (2006.01) | |
| B29K 23/00 | (2006.01) | |

(52) U.S. Cl.
CPC ............ *A61K 8/0229* (2013.01); *A61K 8/342* (2013.01); *A61K 8/345* (2013.01); *A61K 8/361* (2013.01); *A61K 8/362* (2013.01); *A61K 8/416* (2013.01); *A61K 8/732* (2013.01); *A61Q 5/12* (2013.01); *B29C 39/003* (2013.01); *A61K 2800/872* (2013.01); *A61K 2800/882* (2013.01); *B29K 2023/14* (2013.01)

(58) Field of Classification Search
CPC ........ A61K 2800/872; A61K 2800/882; A61K 8/0216; A61K 8/0229; A61K 8/342; A61K 8/345; A61K 8/361; A61K 8/362; A61K 8/416; A61K 8/732; A61K 8/922; A61Q 5/12

See application file for complete search history.

(56) References Cited

U.S. PATENT DOCUMENTS

| | | | | |
|---|---|---|---|---|
| 4,808,322 A | * | 2/1989 | McLaughlin ........ | C11D 3/2013 510/151 |
| 2014/0186284 A1 | * | 7/2014 | Sha ...................... | A61K 8/8176 424/70.13 |
| 2015/0111802 A1 | * | 4/2015 | Constantine ........... | A61K 8/463 510/120 |
| 2015/0359722 A1 | | 12/2015 | Thomas et al. | |
| 2017/0181951 A1 | | 6/2017 | Terrisse et al. | |
| 2018/0289608 A1 | | 10/2018 | Constantine et al. | |

FOREIGN PATENT DOCUMENTS

| | | | |
|---|---|---|---|
| EP | 0823252 A2 | 2/1998 | |
| FR | 3068243 A1 | 1/2019 | |
| WO | 2006067400 A1 | 6/2006 | |
| WO | 2011071964 A1 | 6/2011 | |
| WO | WO-2018015759 A1 * | 1/2018 | ............. C11D 9/265 |
| WO | 2019/001940 A1 | 1/2019 | |
| WO | 2019/038547 A1 | 2/2019 | |

OTHER PUBLICATIONS

Piriyaprasarth et al. (Thai Journal of Agricultural Science 2011;44(5):35-41). (Year: 2011).*
Loden and Maibach (Treatment of Dry Skin Syndrome 2012 p. 244). (Year: 2012).*
Smolinske, SC. (CRC Handbook of Food, Drug, and Cosmetic Excipients 2018; 1 page). (Year: 2018).*
Rhein, L. (Handbook for Cleaning/Decontamination of Surfaces 2007; 305-369) (Year: 2007).*
Schmitt, W.H. (Chemistry and Technology of the Cosmetics and Toiletries Industry 1st Edition 2012; pp. 16-17) (Year: 2012).*

\* cited by examiner

*Primary Examiner* — Ernst V Arnold

(74) *Attorney, Agent, or Firm* — Lorenz & Kopf, LLP

(57) ABSTRACT

The present disclosure relates to a solid hair cosmetic composition comprising—based on the total weight of the cosmetic composition—about 30.0 to about 60.0% by weight of at least one polyhydric alcohol, and optionally: about 0.1 to about 15.0% by weight of at least one cationic surfactant, about 0.1 to about 20.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and about 0.1 to about 40.0% by weight of at least one polysaccharide, as well as production and application methods and uses thereof.

11 Claims, No Drawings

SOLID HAIR COSMETIC COMPOSITION

CROSS-REFERENCE TO RELATED APPLICATION

This application claims priority to German Patent Application No. 10 2019 210 155.0, filed Jul. 10, 2019, which is incorporated herein by reference in its entirety.

TECHNICAL FIELD

The notification describes solid cosmetic compositions based on higher amounts of polyols, in particular solid conditioner compositions which dissolve in contact with water. Which solid cosmetic compositions may contain other ingredients such as surfactants, polysaccharides, fatty alcohols and/or fatty acid(s). The notification further describes processes for the preparation of solid cosmetic compositions and their use for conditioning mainly human hair, but also the skin of the human body.

BACKGROUND

Surfactant-containing products for conditioning primarily human hair, but also the skin of the human body, have been known for a long time and are offered on the market mainly in liquid or paste form in suitable packaging. End users take the required amount of product from the packaging during use and dispose of it after emptying. Compared to certain conditioners sold in solid form, such products offer the user the advantage of easy and quick handling, which is why they dominate the market today. However, this advantage is achieved by accepting certain disadvantages, which are discussed below. In most cases, the packaging of the described products in liquid or paste form includes non-recyclable plastic, which is a serious problem from an environmental point of view in view of the constantly growing amount of plastic waste.

Another problem is that previous products usually contain higher quantities of water or water/solvent mixtures, which means that the products have a larger volume and, possibly of greater importance from a transport point of view, a relatively high weight. This is disadvantageous for several reasons. In times of increasing water scarcity, resources should be saved. An undesirable, increased transport volume associated with large-volume heavy products is also important from an environmental and cost perspective. Another interesting point is that worldwide travel activity is constantly increasing. Consumers are therefore increasingly interested in cosmetic products that are easy to transport due to their low weight and volume. This is particularly relevant with regard to air travel, as larger containers containing liquids are generally excluded from being carried in an aircraft cabin, so that a passenger travelling only with hand luggage often finds himself in the situation, due to the cosmetics products that dominate the market today, of not being able to take his preferred product selection with him or having to decant the corresponding products into smaller containers first, which, however, is generally accompanied by an even greater volume of packaging material.

The provision of alternative product forms with lower water content, which are contained in more environmentally friendly, for example recyclable, packaging to save space, is therefore an important goal in the formulation of improved, contemporary and sustainable cosmetic products.

Fixed conditioner compositions have been known for some time and occupy a market niche. Although they have a very low water or solvent content in general and are often packaged with little material, many people find them uncomfortable to handle because an incipient piece of conditioner is difficult to transport, often partially dissolves when placed near a shower or bathtub or next to the sink, which is also inefficient, and makes the sink or other storage location look unattractive due to conditioner residue, and because conditioner pieces have a tendency to slip out of the user's hand.

Another disadvantage with known solid conditioner formulations, especially with rather small conditioner pieces, is that it takes some time for enough of the conditioner piece to dissolve to achieve the desired amount of foam and the desired conditioning effect. On the one hand, this is usually undesirable for users because of the additional time required, and on the other hand it can be associated with higher water consumption for personal hygiene, as many users do not turn off the water flow of the shower or tap during conditioning. From this point of view, it does not make sense to market known conditioner formulations, especially in miniaturized form of a known piece of conditioner, as their dissolution is too slow as the formulations of these conditioners are not optimized for marketing in single application portions.

BRIEF SUMMARY

In view of the problems and requirements described above, the inventors have therefore set themselves the task of providing formulations and manufacturing processes suitable for solid cosmetic conditioning agents which, by their nature, can be packaged in individual application portions, as well as processes for their manufacture and uses. In their intensive research efforts, the inventors have established several measures that can contribute to this suitability. Thus, the task of the present disclosure is solved by the formulation of procedures and uses described in detail below:

The present disclosure is exemplified by:

an exemplary solid hair cosmetic composition comprising—based on the total weight of the cosmetic composition—

(a) about 30.0 to about 60.0% by weight of at least one polyhydric alcohol, and optionally:

(b) about 0.1 to about 15.0% by weight of at least one cationic surfactant, (c) about 0.1 to about 20.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and (d) about 0.1 to about 40.0% by weight of at least one polysaccharide.

An exemplary solid hair cosmetic composition comprises—based on the total weight of the cosmetic composition—

(a) about 30.0 to about 60.0% by weight of at least one polyhydric alcohol, (b) about 0.1 to about 15.0% by weight of at least one cationic surfactant, (c) about 0.1 to about 10.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and (d) about 0.1 to about 40.0% by weight of at least one polysaccharide.

An exemplary solid hair cosmetic composition comprises—based on the total weight of the cosmetic composition—:
(ai) from more than about 30.0% to about 60.0% by weight of at least one polyhydric alcohol.

An exemplary solid hair cosmetic composition comprises—based on the total weight of the cosmetic composition—:
(ai) about 32.0 to about 50.0% by weight of at least one polyhydric alcohol.

An exemplary solid hair cosmetic composition comprises—based on the total weight of the cosmetic composition—
(ai) about 32.0 to about 40.0% by weight of at least one polyhydric alcohol.

In an exemplary solid hair cosmetic composition, the polyhydric alcohol a) comprises or consists of glycerol and/or propylene glycol.

An exemplary solid hair cosmetic composition includes glycerol as polyhydric alcohol a).

An exemplary solid hair cosmetic composition includes glycerol and propylene glycol as polyhydric alcohol a).

An exemplary solid hair cosmetic composition comprises as cationic surfactant b) at least one compound from the following group:
(i) Alkylquats,
(ii) Esterquats,
(iii) quaternary imidazolines,
(iv) Amidoamines and/or cationized Amidoamines and
(v) Mixtures thereof.

An exemplary solid hair cosmetic composition includes at least one cationic surfactant b) from group i.

An exemplary solid hair cosmetic composition, includes $C_8$-$C_{30}$-alkyl-tri-$C_1$-$C_4$-alkylammonium salts, preferably $C_8$-$C_{24}$-alkyltrimethylammonium salts, especially preferably lauryltrimethylammonium salts, cetyltrimethylammonium salts, stearyltrimethylammonium salts, behene-trimethylammonium salts and/or mixtures thereof, especially the chloride, methosulphate and/or ethosulphates of these cationic surfactants.

An exemplary solid hair cosmetic composition comprises cationic surfactant salts known under the INCI designation "Cetrimonium" and/or "Behentrimonium".

An exemplary solid hair cosmetic composition comprises at least one cationic surfactant b) from group iii, in particular quaternium-87.

An exemplary solid hair cosmetic composition, comprises from about 0.5 to about 10% by weight of at least one cationic surfactant b), preferably from about 0.5 to about 5% by weight, and more preferably from about 1 to about 4% by weight (based on the total weight of the cosmetic composition).

In an exemplary solid hair cosmetic composition, component c) comprises at least one saturated or unsaturated, branched or unbranched $C_8$-$C_{30}$ alcohol, in particular cetyl alcohol, stearyl alcohol, or mixtures thereof.

In an exemplary solid hair cosmetic composition, component c) comprises saturated or unsaturated, branched or unbranched $C_8$-$C_{30}$ carboxylic acids and/or salts thereof, preferably $C_{10}$-$C_{22}$ carboxylic acids and/or salts thereof.

In an exemplary solid hair cosmetic composition component c) comprises coco acids, lauric acid, myristic acid, palmitic acid, stearic acid, behenic acid, oleic acid and mixtures thereof and/or the salts thereof.

In an exemplary solid hair cosmetic compositioncomponent c) comprises palmitic acid and/or stearic acid and mixtures thereof, and/or cetyl alcohol and/or stearyl alcohol.

In an exemplary solid hair cosmetic composition, component c) comprises palmitic acid, stearic acid and cetyl alcohol.

An exemplary solid hair cosmetic composition comprises about 0.5 to about 15%, preferably about 2 to about 15%, and more preferably about 5 to about 12%, by weight of component c) (based on the total weight of the cosmetic composition).

In an exemplary solid hair cosmetic composition, the polysaccharide d) comprises at least one starch and/or at least modified starch and/or at least one dextrin.

In an exemplary solid hair cosmetic composition, the polysaccharide d) comprises at least one starch obtained from natural sources.

In an exemplary solid hair cosmetic composition, the polysaccharide d) comprises at least one of corn, rice, potato or tapioca starch.

In an exemplary solid hair cosmetic composition, the polysaccharide d) includes a corn starch.

In an exemplary solid hair cosmetic composition, the polysaccharide d) includes a dextrin.

In an exemplary solid hair cosmetic composition, the dextrin is maltodextrin.

In an exemplary solid hair cosmetic composition, the polysaccharide d) includes a modified starch.

In an exemplary solid hair cosmetic composition, the modified starch is hydroxypropyl starch phosphate.

In an exemplary solid hair cosmetic composition, the polysaccharide d) contains or consists of a corn starch, maltodextrin and starch hydroxypropyl starch phosphate.

In an exemplary solid hair cosmetic composition, the polysaccharide d) is a maize starch.

In an exemplary solid hair cosmetic composition, the maize starch is *Zea Mays* (corn) starch.

An exemplary solid hair cosmetic composition, includes about 1 to about 30%, preferably about 5 to about 25%, and more preferably about 10 to about 25%, by weight of component d) (based on the total weight of the cosmetic composition).

An exemplary solid hair cosmetic composition, further as cationic polymer, based on the total weight of the cosmetic composition, about 0.01 to about 5.00% by weight of at least one cationic surfactant.

An exemplary solid hair cosmetic composition, further including—based on the total weight of the cosmetic composition—about 0.1 to about 5.00% by weight, preferably about 0.1 to about 3% by weight and more preferably about 0.1 to about 1% by weight, of at least one cationic polymer.

An exemplary solid hair cosmetic composition, includes as a cationic polymer at least one cationic polysaccharide polymer obtainable from guar, *cassia* and/or inulin.

An exemplary solid hair cosmetic composition includes hydroxypropyltrimonium inulin as the cationic polymer.

An exemplary solid hair cosmetic composition, further includes—based on the total weight of the cosmetic composition—about 0.001 to about 0.01% by weight of at least one bittering agent, preferably a compound known under the INCI designation denatonium benzoate.

An exemplary solid hair cosmetic composition, further includes—based on the total weight of the cosmetic composition—about 0.01 to about 20.0% by weight of at least one oil, fat and/or wax component, preferably a naturally occurring oil, fat or wax.

An exemplary solid hair cosmetic composition includes vegetable oils and/or vegetable butters, An exemplary solid hair cosmetic composition includes Shea Butter (INCI designation: Butyrospermum Parkii (Shea) Butter).

An exemplary solid hair cosmetic composition, includes apricot kernel oil, argan oil, jojoba oil, manila oil, almond oil, olive oil, coconut oil and/or sunflower oil.

An exemplary solid hair cosmetic composition, further includes one or more plant extracts.

An exemplary solid hair cosmetic composition further includes citric acid, lactic acid, malic acid and/or glycolic acid, especially citric acid and/or lactic acid.

An exemplary solid hair cosmetic composition further includes sodium bicarbonate.

An exemplary solid hair cosmetic composition includes water in an amount up to about 25% by weight (based on the weight of the composition).

An exemplary solid hair cosmetic composition is provided in the form of a pen or piece.

An exemplary solid hair cosmetic composition is provided in the form of a stick.

An exemplary solid hair cosmetic composition has a Shore AO hardness value of about 5 to about 20.

An exemplary solid hair cosmetic composition has a Shore AO hardness value of about 5 to about 15.

An exemplary solid hair cosmetic composition includes water in an amount up to about 25% by weight, preferably about 20% and more preferably about 15% by weight (based on the weight of the composition).

An exemplary solid hair cosmetic composition is provided in the form of a multiple use piece.

An exemplary solid hair cosmetic composition is provided in the form of a single use piece.

An exemplary solid hair cosmetic composition has a Shore AO hardness value of about 15 to about 35.

An exemplary solid hair cosmetic composition has with a Shore AO hardness value of about 20 to about 30.

An exemplary solid hair cosmetic composition includes water in an amount up to about 15% by weight, preferably about 12.5% and more preferably about 10% by weight (based on the weight of the composition).

An exemplary solid hair cosmetic composition is used for the cleansing and/or care of human skin and/or human hair.

An exemplary solid hair cosmetic composition is provided in the form of a conditioning agent.

An exemplary solid hair cosmetic composition is used for the care of human hair, such as for use after hair cleansing as a leave-on or rinse-off composition.

An exemplary process for preparing the solid hair conditioning composition includes:
mixing all ingredients with sufficient heat and agitation to ensure that all ingredients are melted and/or evenly distributed to form a resulting mixture, and
allowing the resulting mixture to cool and solidify.

An exemplary process for preparing the solid hair conditioning composition includes:
mixing all ingredients with sufficient heat and agitation to ensure that all ingredients are melted and/or evenly distributed to form a resulting mixture,
pouring the resulting mixture into a pin/piece mould, and allowing the mixture to cool and solidify.

An exemplary process for preparing the solid hair conditioning composition includes:
mixing all ingredients with sufficient heat and agitation to ensure that all ingredients are melted and/or evenly distributed to form a resulting mixture,
pouring the resulting mixture into a mould, and
allowing the mixture to cool and solidify.

An exemplary method for treating hair, such as for conditioning hair, includes mixing the solid hair cosmetic composition with water and applying the mixture of the composition and water to the hair, or applying a stick or piece of the solid hair cosmetic composition directly to wet hair and working it in.

In an exemplary embodiment, the solid hair cosmetic composition is used for treating, preferably conditioning, the hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure thus concerns a solid hair cosmetic composition comprising—based on the total weight of the cosmetic composition—
a) About 30.0 to about 60.0% by weight of at least one polyhydric alcohol, and optionally:
b) about 0.1 to about 15.0% by weight of at least one cationic surfactant,
c) about 0.1 to about 20.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and
d) about 0.1 to about 40.0% by weight of at least one polysaccharide.

Such a formulation offers the right properties for single application portions, especially with regard to their dissolving behaviour during use.

The present disclosure further relates to a solid hair cosmetic composition as described above, comprising—based on the total weight of the cosmetic composition—
a) About 30.0 to about 60.0% by weight of at least one polyhydric alcohol,
b) about 0.1 to about 15.0% by weight of at least one cationic surfactant,
c) about 0.1 to about 10.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and
d) about 0.1 to about 40.0% by weight of at least one polysaccharide.

The compositions as contemplated herein are solid at 25° C. Solid compositions within the meaning of the present application are three-dimensional, dimensionally stable entities which are not liquid or gaseous, that is to say, which retain their external shape even without a surrounding vessel. However, the term "solid" does not imply anything about density or elasticity or other physical properties, so that jellies, brawn, butter etc. can also be solid as contemplated herein as long as they are dimensionally stable at 25° C.

Such a formulation offers the right properties for single application portions, especially with regard to their dissolving and foaming behaviour during use. The high concentrations of the active substances in such a composition are associated with the advantages that few resources are consumed during production and transport and that the products, even after they have reached the hands of a consumer via the trade, can be easily transported without great effort or restrictions, whether to the gym or on a flight.

The present disclosure further relates to a solid hair cosmetic composition as described above, comprising (based on the total weight of the cosmetic composition):
ai) about 30.0 to about 60.0% by weight of at least one polyhydric alcohol.

Polyhydric alcohols are mostly well tolerated by the skin and as solvents they ensure that the solid cosmetic compositions available with them are not too solid or too difficult or slow to dissolve. In the defined concentration range, these advantageous properties become particularly apparent.

The present disclosure also relates to a solid hair cosmetic composition as described above, containing as polyhydric alcohol b) alditols such as mannitol, isomalt, lactitol, sorbitol and xylitol, threit, erythritol and arabitol, 1.2-propylene glycol, 1.3-butylene glycol, dipropylene glycol, glycerol and/or diglycerol, preferably glycerol. As contemplated herein, compositions preferably contain glycerol in the quantities mentioned above.

The present disclosure further relates to a solid hair cosmetic composition as previously described, comprising or including glycerol as polyhydric alcohol a).
more than about 30.0 to about 60.0% by weight of at least one polyhydric alcohol, preferably about 32.0 to about 50.0% by weight of at least one polyhydric alcohol.

The present disclosure further relates to a solid hair cosmetic composition as described above, comprising (based on the total weight of the cosmetic composition):
ai) more than about 30.0 to about 60.0% by weight, preferably more than about 30.0 to about 50.0% by weight, in particular preferably more than about 30.0 to about 40.0% by weight, of at least one polyhydric alcohol.

In the defined concentration range, the advantageous properties described above become even more apparent.

The present disclosure further relates to a solid hair cosmetic composition as described above, comprising (based on the total weight of the cosmetic composition):
b) about 0.1 to about 15.0% by weight of at least one cationic surfactant.

Cationic surfactants carry a positive charge in their hydrophilic part. This positive charge causes the surfactant molecules to attach themselves to the negatively charged skin and hair surface. In this way they neutralize the charge, prevent the hair from flying, have a smoothing effect, increase hair shine and improve wet comb-ability. They are primarily used in conditioners, hair conditioners and hair treatments, rarely in shampoos. In addition, cationic surfactants have a co-conserving effect in cosmetic products due to their bactericidal effect, i.e. an inhibiting effect on bacteria.

In principle, all cationic surface-active substances suitable for use on the human body are suitable as cationic surfactants in compositions as contemplated herein. These are exemplified by at least one water-solubilizing, cationic group, such as a quaternary ammonium group, or by at least one water-solubilizing, cationizable group, such as an amine group and furthermore at least one lipophilic alkyl group with about 6 to 30 C atoms, or also by at least one imidazole group or at least one imidazylalkyl group.

In general, cationic surfactants are divided into groups according to their structural characteristics. Particularly suitable for use in the compositions as contemplated herein are cationic surfactants a) from at least one of the groups of alkylquats, esterquats, quaternary imidazolines, amidoamines and/or cationized amidoamines.

The present disclosure further relates to a solid hair cosmetic composition as previously described, comprising as cationic surfactant b) at least one compound from the following group of the:
i. Alkylquats,
ii. Esterquats,
iii. quaternary imidazolines,
iv. Amidoamines and/or cationized Amidoamines and
v. Mixtures thereof.

These specifically named cationic surfactants have shown a conditioning effect in the compositions as contemplated herein which is perceived as particularly pleasant.

Especially preferred compositions as contemplated herein contain as cationic surfactants a)
quaternary ammonium compounds (alkylquats) with at least one $C_8$-$C_{24}$ alkyl radical,
Esterquats and
Amidoamines each having at least one $C_8$-$C_{24}$ acyl group and mixtures thereof.

Quaternary ammonium compounds with at least one $C_8$-$C_{24}$ alkyl radical are particularly preferred ammonium halides, especially chlorides, and ammonium alkyl sulphates, such as methosulphates or ethosulphates, such as $C_8$-$C_{24}$ alkyl trimethylammonium chlorides, $C_8$-$C_{24}$ dialkyldimethylammonium chlorides and $C_8$-$C_{24}$ trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27, Quaternium-83, Quaternium-87 and Quaternium-91. The alkyl chains of the surfactants mentioned above preferably have about 8 to 24 carbon atoms.

Esterquats are cationic surfactants which contain both at least one ester function and at least one quaternary ammonium group as a structural element and furthermore at least one $C_8$-$C_{24}$ alkyl radical or $C_8$-$C_{24}$ acyl radical. Preferred esterquats are quaternized ester salts of fatty acids with triethanolamine, quaternized ester salts of fatty acids with diethanolalkylamines and quaternized ester salts of fatty acids with 1.2-dihydroxypropyl dialkylamines Such products are sold under the trademarks Stepantex®, Dehyquart® and Armocare®. N,N-bis(2-palmitoyloxyethyl)dimethylammonium chloride, distearoylethyl dimonium methosulfates and distearoylethyl hydroxyethylmonium methosulfates are preferred examples of such esterquats.

The alkylamidoamines are usually produced by amidation of natural or synthetic $C_8$-$C_{24}$ fatty acids and fatty acid sections with di-($C_1$-$C_3$)alkylaminoamines Compounds from this substance group which are particularly suitable as contemplated herein are for example the compounds known under the INCI designations stearamidopropyl dimethylamine, behenamidopropyl dimethylamine and/or brassicamidopropyl dimethylamine. Stearamidopropyl dimethylamine is particularly preferred.

Alkylamidoamines are usually produced by amidation of natural or synthetic C8-C24 fatty acids and fatty acid sections with di-(C1-C3)alkylaminoamines A compound from this substance group which is particularly suitable as contemplated herein is stearamidopropyldimethylamine.

The present disclosure further relates to a solid hair cosmetic composition as described above, comprising at least one cationic surfactant b) from group iii, in particular quaternium-87.

The present disclosure further relates to a solid hair cosmetic composition as described above, comprising at least one cationic surfactant b) from group i, preferably $C_8$-$C_{30}$ alkyl tri-$C_1$-$C_4$ alkylammonium salts and in particular cationic surfactant salts known under the INCI designation "Cetrimonium" and/or "Behentrimonium".

These specifically named cationic surfactant salts have shown in the compositions as contemplated herein a conditioning effect which is perceived as particularly pleasant.

Compositions preferred as contemplated herein contain at least one cationic surfactant in a total amount of about 0.1 to about 15% by weight, preferably about 0.5 to about 10% by weight, particularly preferably about 1 to about 5% by weight, each based on the weight of the composition.

In addition to conditioning agents, the compositions as contemplated herein can also be cleaning agents. Also contains cleaning agents preferred as contemplated herein—
  contains at least one cationic surfactant, preferably in a total amount of about 0.1 to about 2% by weight, more preferably about 0.2 to about 1% by weight and particularly preferably about 0.3 to about 0.5% by weight, each based on the weight of the composition, and
  at least one further surfactant selected from anionic, amphoteric, zwitterionic and/or non-ionic surfactants, preferably in a total amount of about 1 to about 40% by weight, more preferably about 2 to about 35% by weight and particularly preferably about 3 to about 30% by weight, each based on the weight of the composition.

The present disclosure further relates to a solid hair cosmetic composition as described above, comprising as component c) at least one saturated or unsaturated, branched or unbranched $C_8$-$C_{30}$ alcohol, in particular cetyl alcohol, stearyl alcohol, or mixtures thereof in the aforementioned amounts.

These compounds have proved to be particularly suitable structure-giving ingredients for the purposes of the present disclosure. They can be used to formulate hair cosmetic compositions of sufficient strength that do not melt too low.

The present disclosure further relates to a solid hair cosmetic composition as described above, comprising as component c) saturated or unsaturated, branched or unbranched $C_8$-$C_{30}$ carboxylic acids and/or their salts, preferably $C_{10}$-$C_{22}$ carboxylic acids and/or their salts and in particular coco acids, lauric acid, myristic acid, palmitic acid, stearic acid, behenic acid, oleic acid as well as mixtures thereof and/or the salts of these acids. Especially suitable are stearic acid and palmitic acid and/or the salts of these acids, especially stearic acid and palmitic acid.

Such a composition has essentially comparable advantages to those previously described in connection with $C_8$-$C_{30}$ alcohols.

Compositions preferred as contemplated herein contain at least one saturated or unsaturated, branched or unbranched C8-C30 alcohol and/or a saturated or unsaturated, branched or unbranched C8-C30 carboxylic acid and/or a salt of a saturated or unsaturated, branched or unbranched C8-C30 carboxylic acid in a total amount of about 0.1 to about 20% by weight, preferably about 1 to about 18% by weight, particularly preferably about 4 to about 15% by weight, in particular about 6 to about 14% by weight; in each case based on the weight of the composition.

The present disclosure further relates to a solid hair cosmetic composition as described above, comprising as component d) at least one polysaccharide.

Polysaccharides suitable for present disclosure d) are composed of more than ten monosaccharide units. Preferred polysaccharides are the starches composed of α-D-glucose units and starch degradation product s such as amylose, amylopectin and dextrins. As contemplated herein, chemically and/or thermally modified starches, e.g. hydroxypropyl starch phosphate, dihydroxypropyl distarch phosphate or the commercial products Dry Flo® are also particularly advantageous. Dextranes and their derivatives, e.g. dextran sulphate, are also preferred. Also preferred are non-ionic cellulose derivatives, such as methyl cellulose, hydroxypropyl cellulose, hydroxypropyl methyl cellulose or hydroxyethyl cellulose, and cationic cellulose derivatives, e.g. the commercial products Celquat® and Polymer JR®, and preferably Celquat® H 100, Celquat® L 200 and Polymer JR® 400 (polyquaternium-10) and polyquaternium-24. Other preferred examples are polysaccharides from fucose units, such as the commercial product Fucogel®.

In the compositions as contemplated herein, the polysaccharides d) are preferably contained in amounts of about 1 to about 40 wt. %, preferably about 5 to about 30 wt. % and particularly preferably about 10 to about 25 wt. %, each based on the total composition.

The present disclosure further relates to a solid hair cosmetic composition as described above, comprehensive:
  at least one starch obtained from natural sources (preferably where the starch obtained from natural sources is preferably from maize, rice, potato or tapioca),
  at least one modified starch, and/or
  at least one dextrin.

The present disclosure also relates to a solid hair cosmetic composition as previously described, containing as polysaccharide d)
i. Starch fractions from corn, potatoes, rice, wheat and/or tapioca and/or
ii. modified starches, preferably hydroxypropyl starch phosphates and/or
iii. Derivatives of starches such as amylose, amylopectin, dextrins and/or maltodextrin.

Especially preferred is a solid hair cosmetic composition, as described above, containing as polysaccharide d)i starch fractions from corn.

Also particularly preferred is a solid hair cosmetic composition, as described above, containing as polysaccharide d)ii. compounds known under the INCI designation Hydroxypropyl Starch Phosphates.

Also particularly preferred is a solid hair cosmetic composition, as described above, containing as polysaccharide d)iii. Maltodextrin.

Particularly preferred is a solid hair cosmetic composition, as described above, containing polysaccharides d) from groups i, ii and iii, preferably starch fractions from maize, compounds known under the INCI designation Hydroxypropyl Starch Phosphates and maltodextrin.

These polysaccharides have proved to be well suited as stabilising agents in the context of the present disclosure claimed here. Their use makes it possible to provide ready-made consumer products that retain their properties and appearance over a long period of time and under various environmental conditions.

The present disclosure further relates to a solid hair cosmetic composition as previously described, further comprising—based on the total weight of the cosmetic composition—about 0.01 to about 5.00% by weight of at least one cationic polymer, preferably at least one cationic polysaccharide polymer obtainable from guar, *cassia* and/or inulin.

Cationic polymers have conditioning properties, i.e. they provide a pleasant skin or hair feel and thus offer added value. They can be used in the context of the present disclosure without significantly affecting the cleaning performance. The specifically named polymers are particularly suitable.

In more detail, suitable cationic care polymers are also to be understood, for example:

- quaternized cellulose polymers, especially polyquaternium-10, as commercially available under the names Celquat® and Polymer JR®,
- hydrophobically modified cellulose derivatives, for example the cationic polymers sold under the trade name SoftCat®,
- cationic alkyl polyglycosides,
- cationized honey, for example the commercial product Honeyquat® 50,
- cationic guar derivatives, in particular those marketed under the trade names Cosmedia® Guar, N-Hance® and Jaguar® distributed products,
- polymeric dimethyldiallylammonium salts and their copolymers with esters and amides of acrylic acid and methacrylic acid, especially polyquaternium-6 and polyquaternium-7. The products commercially available under the names Merquat® 100 (poly(dimethyldiallylammonium chloride)) and Merquat®550 (Dimethyldiallylammonium chloride-acrylamide copolymer) are examples of such cationic polymers,
- Copolymers of vinylpyrrolidone with quaternized derivatives of dialkylaminoalkyl acrylate and -methacrylate, such as those quaternized with diethyl sulphate Vinylpyrrolidon-Dimethylaminoethylmethacrylat-Copolymere. Such compounds are commercially available under the names Gafquat®734 and Gafquat®755,
- Vinylpyrrolidone-vinylimidazolium methochloride copolymers, as offered under the names Luviquat® FC 370, FC 550, FC 905 and HM 552,
- quaternized polyvinyl alcohol,
- and the products listed under the designations Polyquaternium 2, Polyquaternium 17, Polyquaternium 18, Polyquaternium-24, Polyquaternium 27, Polyquaternium-32, Polyquaternium-37, Polyquaternium 74 and Polyquaternium 89 known polymers.

Particularly preferred cationic polymers are quaternized cellulose polymers, hydrophobically modified quaternized cellulose polymers, cationic guar derivatives and/or cationic polymers based on acrylic acid (derivative), which are particularly preferably selected from the polymers known under the INCI designations guar hydroxypropyltrimonium chlorides, polyquaternium-6, polyquaternium-7, polyquaternium-10, polyquaternium-37 and/or polyquaternium-67. Cationic polysaccharide polymers, especially guar hydroxypropyltrimonium chloride, are particularly preferred for the purposes of the present disclosure.

Furthermore, cationic polymers, which are obtained from natural sources (besides guar), such as a cationic inulin polymer, are particularly preferred. A content of these specific polymer types in the mixture of active ingredients as contemplated herein is not only beneficial for the improvement of hair care properties, but it was also found that polymers in combination with other cationic polymers do not cause an over conditioning effect even after regular use.

Inulin is a polysaccharide belonging to the group of fructans. In addition to a terminal glucose building block, the chain contains up to about 60 fructose monomers, each of which is linked via β-2,1-glycosidic bonds. Inulin may be obtained from the leaves, roots, fruits and/or flowers of composites and/or umbellifers, such as Jerusalem artichokes, chicory, artichokes and/or parsnips.

Cationic inulin polymers particularly suitable as contemplated herein are cationically modified by reacting hydroxyl groups of the fructose building blocks with reactive quaternary ammonium compounds. Suitable quaternary ammonium compounds are preferably compounds of the following formula $$N^+(R^1R^2R^3R^4)X^-$$

in which $R^1$, $R^2$ and $R^3$ are methyl or ethyl groups and $R^4$ is an epoxy-$R^5$— or a halohydrin group Y—$CH_2$—CH(OH)—$R^5$—, in which $R^5$ is a $C_1$-$C_3$ alkylene group, Y is a halide and X is an anion such as Cl—, Br—, I— or HSO4. Particularly suitable cationic inulin polymers b) for the purposes of the present disclosure correspond to the formula $$R-O-CH_2-CH(OH)-R^5-N^+(R^1R^2R^3)X^-,$$

wherein R is inulin and the other residues have the same meaning as above.

In a particularly preferred embodiment, the compositions as contemplated herein contain cationic inulin polymers cationically modified with cationic hydroxy-$C_1$-$C_3$-alkyl-trialkylammonium groups, in particular with hydroxypropyltrimethylammonium groups. Within this embodiment, cationic inulin polymers known and commercially available under the INCI designation Hydroxypropyltrimonium Inulin are preferred.

The degree of cationic substitution of cationic inulin polymers, especially of cationic inulins known under the INCI designation Hydroxypropyltrimonium Inulin, can be varied and adjusted as required. For use in the cosmetic compositions as contemplated herein, it has been shown to be particularly preferred when such cationically modified inulin polymers exhibit a higher degree of cationic modification (higher degree of cationic substitution), because this allows better coacervate formation and ultimately better care performance to be achieved in the compositions.

In a particularly preferred embodiment, the cationic inulin polymer contained in the cosmetic compositions as contemplated herein has a cationic charge density > about 1.5 meq/g, more preferably > about 2.0 meq/g, particularly preferably > about 2.5 meq/g, very preferably > about 3.0 meq/g and especially > about 3.5 meq/g. Within this version it is particularly preferred if cationic inulin polymers known under the INCI designation Hydroxypropyltrimonium Inulin b) have a cationic charge density > about 1.5 meq/g, more preferably > about 2.0 meq/g, particularly preferably > about 2.5 meq/g, very particularly preferably > about 3.0 meq/g and particularly > about 3.5 meq/g.

In another particularly preferred version, the cationic inulin polymer b) contained in the cosmetic compositions as contemplated herein has an average molar mass of about 2,000 to about 50,000 g/mol, more preferably about 2,500 to about 40,000 g/mol, particularly preferably about 3,000 to about 30,000 g/mol, very preferably about 3,500 to about 20,000 g/mol and in particular about 4,000 to about 10,000 g/mol. Within this version it is particularly preferred if cationic inulin polymers known under the INCI designation Hydroxypropyltrimonium Inulin b) have an average molar mass of about 2,000 to about 50,000 g/mol, more preferably about 2,500 to about 40,000 g/mol, particularly preferably about 3,000 to about 30,000 g/mol, very preferably about 3,500 to about 20,000 g/mol and particularly about 4,000 to about 10,000 g/mol.

The cationic inulin polymer(s)—preferably compounds known under the INCI designation Hydroxypropyltrimonium Inulin—are preferably used in the cosmetic cleansing compositions as contemplated herein in an amount of about 0.01 to about 5.00 wt.-%, more preferably about 0.02 to about 4.00% by weight, particularly preferably about 0.03 to about 3.00% by weight, very particularly preferably about 0.04 to about 2.50% by weight and in particular from about 0.05 to about 2.00% by weight (based on the total weight of the cleansing compositions).

In a further preferred embodiment, the cosmetic compositions as contemplated herein contain, instead of the cationic inulin polymer or in addition to the cationic inulin polymer, at least one other cationic polymer selected from cationic polymers of natural origin, preferably from cationic polygalactomannan derivatives.

Galactomannans are polysaccharides including combinations of mannose and galactose monomers in different contents. In it, the mannose units are connected to each other via β(1-4)-glycosidic bonds; the galactose units via α(1-6)-bonds. The ratio of mannose to galactose monomers varies according to the type and origin of the plant and the temperature at which it was grown. In Greek fenugreek gum, the mannose-galactose ratio is about 1:1 (corresponding to one monomer of mannose to one monomer of galactose); in guar gum about 2:1; in tara gum about 3:1; in locust bean gum about 4:1 and in *cassia* gum about 5:1. All galactomannans from these sources are suitable for cationic modification and use as polymers in cosmetic compositions as contemplated herein. Guar gum and/or *cassia* gum are particularly suitable for use in cosmetic products as contemplated herein.

Like the cationic inulin polymers, the galactomannans, preferably galactomannans from the aforementioned sources, can be cationically modified by reacting the hydroxyl groups of the galactomannan polymers with reactive quaternary ammonium compounds. Suitable quaternary ammonium compounds are preferably compounds of the following formula $$N^+(R^1R^2R^3R^4)X^-$$ 

in which $R^1$, $R^2$ and $R^3$ are methyl or ethyl groups and $R^4$ is an epoxy-$R^5$— or a halohydrin group Y—$CH_2$—CH(OH)—$R^5$—, in which $R^5$ is a $C_1$-$C_3$ alkylene group, Y is a halide and X is an anion such as Cl—, Br—, I— or HSO4. Particularly suitable cationic galactomannane polymers within the meaning of the present disclosure correspond to the formula $$R\text{—}O\text{—}CH_2\text{—}CH(OH)\text{—}R^5\text{—}N^+(R^1R^2R^3)X^-,$$ 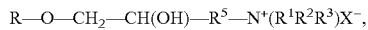

wherein R is the respective galactomannan and the other radicals have the same meaning as above.

In a particularly preferred embodiment, the compositions as contemplated herein therefore contain cationic galactomannan polymers cationically modified with cationic hydroxy-$C_1$-$C_3$-alkyl-trialkylammonium groups, in particular with hydroxypropyltrimethylammonium groups. Within this version, galactomannan polymers which have been cationically modified with cationic hydroxy-$C_1$-$C_3$-alkyl-trialkylammonium groups, in particular with hydroxypropyltrimethylammonium groups, and which are derived from guar gum and/or *cassia* gum are particularly preferred.

In a particularly preferred embodiment, the cosmetic compositions as contemplated herein contain as a polygalactomannan derivative at least one of the compounds known under the INCI designations Guar Hydroxypropyltrimonium Chloride, Hydroxypropyl Guar Hydroxypropyltrimonium Chloride and/or *Cassia* Hydroxypropyltrimonium Chloride.

Guar and *Cassia* polymers known under these INCI designations are commercially available from various suppliers, for example under the designations Jaguar®, N-Hance®, Polycare®, Clearhance®, Activsoft®, Guarquat®, Vida-Care®. Jaguar® C-162, Jaguar® C500, Jaguar® Styl 100, N-Hance® 3196, N-Hance® HPCG 1000, Activsoft® C17, Guarquat® C130 KC, Guarquat® CP500 KC, Vida-Care® GHTC and/or Polycare® Split Therapy are specific examples of cationic polymers of natural origin that are particularly suitable as contemplated herein.

Cationic polymers suitable as contemplated herein are preferably used in the cosmetic compositions as contemplated herein (based on their total weight) in amounts of about 0.01 to about 2.00% by weight, more preferably about 0.02 to about 0.90% by weight, particularly preferably about 0.03 to about 0.80% by weight, very particularly preferably about 0.04 to about 0.70% by weight and in particular about 0.05 to about 0.60% by weight.

Polysaccharides suitable for present disclosure are composed of more than ten monosaccharide units. Preferred polysaccharides are the starches composed of α-D-glucose units and starch degradation product s such as amylose, amylopectin and dextrins. As contemplated herein, chemically and/or thermally modified starches are particularly advantageous, e.g. hydroxypropyl starch phosphate, dihydroxypropyl distarch phosphate or the commercial products Dry Flo®. Dextranes and their derivatives, e.g. dextran sulphate, are also preferred. Also preferred are non-ionic cellulose derivatives, such as methyl cellulose, hydroxypropyl cellulose, hydroxypropyl methyl cellulose or hydroxyethyl cellulose, and cationic cellulose derivatives, e.g. the commercial products Celquat® and Polymer JR®, and preferably Celquat® H 100, Celquat® L 200 and Polymer JR® 400 (polyquaternium-10) and polyquaternium-24. Other preferred examples are polysaccharides from fucose units, such as the commercial product Fucogel®.

The present disclosure further relates to a solid hair cosmetic composition as described above, further comprising—based on the total weight of the cosmetic composition—about 0.01 to about 20.0% by weight of at least one oil, fat and/or wax component, preferably a naturally occurring oil, fat or wax.

These are caring substances that help to keep both the skin and hair structure healthy. The defined concentration range makes it possible to use this care effect but at the same time to exclude noticeable greasiness after application of an appropriate composition. Naturally occurring raw materials have the advantage that they grow again and can therefore be used sustainably. This aspect is also becoming increasingly important to many users.

It has been found that vegetable butters with a melting range of from about 20° C. to about 35° C. are particularly suitable for incorporation into cosmetic compositions as contemplated herein.

Accordingly, vegetable butters with a melting point in the range from about 20° C. to 35° C., such as Shea butter (INCI designation), are particularly preferred: Butyrospermum Parkii (Shea) Butter), Mango Butter (INCI designation: *Mangifera indica* (Mango) Seed Butter), Murumuru Butter (INCI designation: *Astrocaryum murumuru* Seed Butter), cocoa butter (INCI designation: *Theobroma cacao* (Cocoa) Seed Butter) and/or Cupuacu Butter (INCI designation: *Theobroma grandiflorum* Seed Butter).

Cupuacu butter (INCI designation) is particularly preferred: *Theobroma Grandiflorum* Seed Butter) and/or Shea Butter (INCI designation: Butyrospermum Parkii (Shea) Butter) and especially preferred is Shea Butter (INCI designation: Butyrospermum Parkii (Shea) Butter).

The at least one vegetable butter (preferably Cupuacu butter and/or Shea butter; in particular shea butter) is used in the cosmetic compositions as contemplated herein preferably in a proportion by weight of about 0.01 to about 10.00% by weight, more preferably of about 0.05 to about 5% by weight, particularly preferably of about 0.10 to about 1% by weight of the total weight of the compositions.

Oils suitable as contemplated herein are preferably perfume oils and/or vegetable triglyceride oils, such as coconut oil, (sweet) almond oil, walnut oil, peach kernel oil, apricot kernel oil, avocado oil, tea tree oil, soy bean oil, cotton seed oil, sesame oil, sunflower oil, tsubaki oil, evening primrose oil, rice bran oil, palm oil, Palm kernel oil, mango kernel oil, cranberry oil, sea buckthorn oil, meadow foam herb oil, thistle oil, macadamia nut oil, grape seed oil, amaranth seed oil, argan oil, bamboo oil, olive oil, Wheat germ oil, pumpkin seed oil, mallow oil, hazelnut oil, safflower oil, corn oil, olive oil, rapeseed oil, canola oil, sasanqua oil, jojoba oil, rambutan oil, manila oil and/or *quinoa* oil.

Particularly preferred are apricot kernel oil, argan oil, jojoba oil, manila oil, macadamia nut oil, pumpkin seed oil, amaranth seed oil, *quinoa* oil, soy bean oil, cotton seed oil, sunflower oil, palm oil, palm kernel oil, linseed oil, almond oil, corn oil, olive oil, rapeseed oil, sesame oil, soy bean oil, thistle oil, wheat germ oil, peach kernel oil, cranberry oil, sea buckthorn oil and/or coconut oil.

Especially preferred are apricot kernel oil, argan oil, jojoba oil, manila oil, almond oil, olive oil, coconut oil and/or sunflower oil.

The oil(s) can be used in the compositions as contemplated herein preferably in a proportion by weight of about 0.01 to about 10%, more preferably about 0.05 to about 7%, more preferably about 0.10 to about 5% by weight of the total weight of the compositions.

The present disclosure further relates to a solid hair cosmetic composition as previously described, further comprising—based on the total weight of the cosmetic composition—about 0.001 to about 0.01% by weight of at least one bittering agent, preferably a compound known under the INCI designation Denatonium Benzoate.

A bitter substance is particularly important in cosmetics, household products etc. which are made up in such a way that their shape, colour, feel etc. appeal to small children or babies and encourage them to play, although swallowing could also occur. A bitter substance prevents this. Denatonium benzoate is an extremely strong bittering agent and is therefore particularly effective even at exceptionally low application concentrations. Furthermore, it is not associated with any known adverse effects.

In addition to the ingredients described above, the cosmetic compositions as contemplated herein may contain at least one active ingredient advantageously selected from the group comprising plant extracts, humectants, protein hydrolysates, perfumes, UV filters, structurants such as maleic acid, dyes for colouring the composition, Active ingredients such as bisabolol and/or allantoin, antioxidants, preservatives such as sodium benzoate or salicylic acid, additional viscosity regulators such as salts (NaCl) or polymers, and pH adjusters such as α- and β-hydroxycarboxylic acids such as citric acid, lactic acid, malic acid, glycolic acid, and/or bases such as alkanolamines and/or sodium hydroxide).

Suitable plant extracts are extracts that can be produced from all parts of a plant. Usually these extracts are produced by extraction of the whole plant. However, in some cases it may be preferable to produce the extracts exclusively from flowers and/or leaves of the plant. Especially suitable are extracts from *Paeonia lactiflora, Rosa damascena* Flower, *Malus domestica* Fruit, *Argania spinosa* Shell Powder, *Laminaria saccharina, Cannabis sativa*, Green Tea, Oak bark, Nettle, *Hamamelis*, Hops, Chamomile, Burdock root, Horsetail, Hawthorn, Lime blossom, Litchi, Almond, Aloe Vera, Spruce needle, Horse chestnut, Sandalwood, juniper, coconut, mango, apricot, lime, wheat, kiwi, melon, orange, grapefruit, sage, rosemary, birch, mallow, cuckooflower, thyme, yarrow, Thyme, lemon balm, cowslip, marshmallow, *ginseng*, ginger root, *Echinacea purpurea, Olea europea, Boerhavia diffusa* roots, *Foeniculum vulgaris* and *Apim graveolens*. The extracts of *Paeonia lactiflora, Rosa damascena* Flower, *Malus domestica* Fruit, *Argania spinosa* Shell Powder, *Laminaria saccharina, Cannabis Sativa*, Green Tea, Nettle, *Hamamelis*, Chamomile, Aloe Vera, *Ginseng, Echinacea purpurea, Olea europea* and/or *Boerhavia diffusa* roots are particularly preferred for use in the compositions as contemplated herein. Water, alcohols and mixtures thereof may be used as extraction agents for the preparation of the above plant extracts. Among the alcohols, lower alcohols such as ethanol and isopropanol, but especially polyhydric alcohols such as ethylene glycol and propylene glycol, both as the sole extracting agent and mixed with water, are preferred. Plant extracts based on water/propylene glycol in a ratio of about 1:10 to about 10:1 have proven to be particularly suitable. The plant extracts can be used both in pure and diluted form. If they are used in diluted form, they usually contain approx. about 2-80% by weight of active substance and the extraction agent or mixture of extraction agents used in their extraction as solvent. The plant extracts can be used in the hair treatment compositions as contemplated herein (based on the total weight of the compositions) preferably in an amount of about 0.01 to about 10% by weight, more preferably of about 0.05 to about 7.5% by weight and especially of about 0.1 to about 5% by weight.

Among suitable pH adjusting agents, particularly preferred for use in the compositions as contemplated herein are citric acid, lactic acid, malic acid, glycolic acid, especially citric acid and/or lactic acid.

The present disclosure further relates to a solid hair cosmetic composition as described above for the cleansing and/or care of human skin and/or human hair.

With such a solid hair cosmetic composition the above described benefits can be achieved on human skin and/or human hair.

The present disclosure further relates to a solid hair cosmetic composition as described above, with a Shore A hardness value of about 10 to 30 and a Shore AO hardness value of about 5 to about 60.

Such a hardness range is perceived as pleasant by users. In this area it is possible to take a small amount of solid hair cosmetic composition for one application from a jar intended for several applications with the hands and without any other aids.

If a Shore A hardness is indicated in the context of this application, it means that the hardness was determined by measurement with a needle with a truncated conical tip, the face of the truncated cone having a diameter of 1.3 millimetres at an angle of 35°. If a Shore AO hardness is specified, this was measured by measuring with a needle with a spherical segment-shaped rounded tip with a radius of the spherical segment of 2.5 mm One durometer was "set" on the product without additional pressure and the maximum value was read. One multiple measurement (at least 3 measurements) was performed in each case and the mean value was given. A manual analogue durometer from Sauter GmbH was used. Unless otherwise expressly described, the instructions enclosed with this device, version 1.2, dated August 2014, which states that it complies with DIN 53505, ASTM D2240 and ISO 868, have been followed.

The present disclosure also relates to a solid hair cosmetic composition as described above for the care of human hair, in particular for use after hair cleansing as a leave-on or rinse-off composition.

The terms 'leave-on' and 'rinse-off' mean that the composition is left in the hair either for a relatively short period of time, such as less than a minute, or for a few minutes or an hour, until it is rinsed out, or that the composition remains in the hair until the next wash, which may be a few days. Both have certain advantages. With a composition that remains on the hair for a long time, the full care potential of all ingredients can be used to a certain extent, whereas a composition that is to be rinsed out again in a short time can also contain ingredients that have a good care effect but whose longer retention in the hair would be unpleasant.

Preferred in terms of the present disclosure are rinse-off compositions.

The present disclosure further relates to a solid hair cosmetic composition as described above in the form of a pen or piece.

As can be seen from the production processes and applications revealed herein, the pen is well suited for multiple use by the user. The present disclosure therefore represents the solid hair cosmetic composition as described above in the form of a multiple use stick.

The piece can be dimensioned in such a way that it can be used either individually or multiple times. Particular preference is given to pieces that are sized to allow the piece to be used only once. The present disclosure therefore provides for the solid hair cosmetic composition as described above in the form of a disposable or reusable piece, preferably in the form of a disposable piece.

These forms of packaging each have certain advantages. One piece still resembles in some ways traditionally used cosmetics and is often preferred by less experimental users. A stick is easier to transport because it is usually fitted with a cap or sleeve and is easier to hold because it can be grasped by its base, sleeve or outer packaging.

As can be seen from the production processes and applications revealed herein, the pen is well suited for multiple use by the user. The present disclosure therefore represents the solid hair cosmetic composition as described above in the form of a multiple use stick.

The piece can be dimensioned in such a way that it can be used either individually or multiple times. Particular preference is given to pieces that are sized to allow the piece to be used only once. The present disclosure therefore provides for the solid hair cosmetic composition as described above in the form of a disposable or reusable piece, preferably in the form of a disposable piece.

The present disclosure further relates to a process for preparing the solid hair conditioning composition as previously described, comprising the process:
a) Mix all ingredients with sufficient heat and agitation to ensure that all ingredients are melted and/or evenly distributed,
b) Allow the resulting mixture to cool and solidify.

Such a process makes an evenly mixed solid hair conditioning composition as described above actually available and allows you to experience its benefits.

The present disclosure further relates to a process for preparing the solid hair conditioning composition as previously described, comprising the process:
a) Mix all ingredients with sufficient heat and agitation to ensure that all ingredients are melted and/or evenly distributed,
b) Pour the resulting mixture into a pin/piece mould,
c) Allow the mixture to cool and solidify.

Such a process makes an evenly mixed solid hair conditioning composition in stick or piece form as described above actually available and its related benefits described above can be experienced.

The present disclosure further relates to a process for preparing the solid hair conditioning composition as previously described, comprising the process:
a) Mix all ingredients with sufficient heat and agitation to ensure that all ingredients are melted and/or evenly distributed,
b) Pour the resulting mixture into a mould,
c) Allow the mixture to cool and solidify.

Such a process makes a uniformly blended solid hair conditioning composition actually available in a specific as described above and makes it possible to experience its related benefits described above.

The present disclosure further relates to a method for treating hair, preferably conditioning hair, in which a solid hair cosmetic composition is mixed with water as described above and applied to the hair or in which a stick or piece is applied directly to wet hair and incorporated.

This procedure makes the advantages described above tangible for a user and thus represents an enrichment not only for personal hygiene and care but also a sensory enrichment.

The present disclosure further relates to a use of a solid hair cosmetic composition as described above for treating, preferably conditioning and/or grooming the hair.

This use makes the advantages described above tangible for a user and thus represents an enrichment not only for personal hygiene and care but also a sensory enrichment.

As can be seen from the previously described designs and their advantages, the process and packaging aspects are important for the present disclosure. They are discussed in more detail below.

In a manufacturing process as contemplated herein, for example, all ingredients are placed in a heatable container, such as, on a laboratory scale, in a suitable vessel in a water bath or on a heating plate, on a production scale rather in a closed and pressurizable vessel, and are mixed and heated, in the recipes as contemplated herein, for example at about 75° C., until all ingredients are sufficiently mixed. In such a process, different temperature steps can also be run. For example, components that can be homogeneously mixed even at a relatively low temperature can be mixed first. This can happen at about 40° C. to about 50° C. It can also be advantageous to mix in certain ingredients at higher temperatures, for example at about 85° C. to about 90° C. For this purpose, a process as contemplated herein may comprise one or more steps in this temperature range. Afterwards, one or more steps can be carried out at a lower temperature again, in which further components are mixed in. Typically, the compositions as contemplated herein solidify at about 65° C., so that certain process steps, such as mixing and extruding the finished mixtures, are not reasonably possible below such a temperature level.

If a composition as contemplated herein is extruded, the available shape can be determined by a shape of the die closing the extruder. The solidifying mixture can be filled into moulds, portioned on a base or produced endlessly and cut and portioned at the nozzle or afterwards.

The compositions as contemplated herein are also suitable for some other forms of packaging not yet described in detail. For example, a stick or pen can be realized. One end of the pen may remain in a wrapper or package during use, so that a user does not have the problem of holding on to a slippery piece of solid cosmetic preparation. The design can be chosen, for example, like a shaving soap, where there is usually a fixed base on one side of the pen and the pen itself is surrounded by a sleeve that can be easily removed by hand, or it can be more similar to a deodorant stick, i.e. include a fixed sleeve also around the outer circumferential surface of the pen as well as a mechanism to gradually advance the pen inside the sleeve so that it always protrudes slightly beyond the opening until it is finally completely worn away by repeated use. The packaging for transport, for example during a journey, is also quite simple with a pen, as a cap surrounding or covering the pen can easily be attached. Pens would be problematic with a conventional conditioner formulation because the material removal on the relatively small surface would be too slow. With the compositions as contemplated herein, they can be easily realized and the speed of material removal during application meets the expectations of the users without, on the other hand, leading to wasteful use through excessive removal.

The extrusion processes described above can also be used to produce interesting shapes reminiscent of injection-moulded biscuits. Thanks to specially shaped dies on the extrusion die, a variety of shapes can be realized, for example a heart or clover shape. An extruded strand thus obtained can then be cut into pieces or slices, providing emotionally appealing small portions of the solid cosmetic compositions as contemplated herein. Similarly, it is possible to roll out an extruded strand or other form of a composition as contemplated herein and then, by punching or cutting, produce pieces that are similar to cookie cutters in terms of shaping properties.

It is also possible to pour the solid cosmetic compositions as contemplated herein into a crucible, for example a glass jar. Since the strength of these compositions is in a range that allows an application portion to be taken manually, without a tool, from a crucible intended for multiple applications. If the composition has been foamed in a crucible during its manufacture, the result is a particularly interesting feeling.

It is also possible to make up solid cosmetic compositions reminiscent of a piece of paper, a foil or a wafer, which brings with it a new and pleasant feeling during application. Since the thickness of the coating is small in this type of packaging, short dissolution times are possible, which accommodates impatient users and does not encourage wasteful use of water. A product packaged in this way may be placed on the market in a packaging unit in which a large number of leaves or flakes are placed in a small carton, possibly subdivided, so that a single withdrawal is possible.

After various designs and their respective advantages were explained in detail, the presentation of exemplary compositions and an exemplary manufacturing process follows.

Detailed exemplary compositions are shown in the following table 1:

TABLE 1

| Group | Ingredients | Active substances contained therein | A | B |
|---|---|---|---|---|
| 1 | Water | Water | 18 | 36.5 |
| 1 | Citric acid monohydrate | Citric acid | 0.25 | 0.25 |

TABLE 1-continued

| Group | Ingredients | Active substances contained therein | A | B |
|---|---|---|---|---|
| 1 | Dehyquart A CA ® | Cetrimonium chloride | 8 | 8 |
| 1 | Glycerine 99.5% | Glycerine | 35 | 35 |
| 1 | Cetearyl alcohol | Cetearyl alcohol | 5 | 2 |
| 1 | Cutina FS 45 | Palmitic acid, stearic acid | 5 | 2 |
| 1 | Cutina GMS-V | Glyceryl stearate | 5 | 2.5 |
| 2 | Agenamalt ® 20.225 Maltodextrin DE15 | Maltodextrin | 1 | 1 |
| 3a | Structure XL ® (28-030A) | Hydroxypropyl starch phosphate | 1.5 | 1.5 |
| 3b | Maisita 9040 ® | Zea Mays- (Corn-) starch | 17.25 | 10 |
| 4 | Cetiol SB 45 ® | Butyrospermum Parkii (Shea) Butter) | 0.5 | 0.5 |
| 4 | Apricot kernel oil, cold pressed | Prunus Armeniaca (apricot) seed oil | 2 | 2 |
| 4 | Perfume Tea Grandiosa 611084 | Perfume (Scent) | 0.5 | 0.5 |
| 4 | Phenoxyethanol, pure | Phenoxyethanol | 1 | 1 |

The exemplary procedure was carried out as follows:

The ingredients were used in the ratio shown in the table above. Dehyquart A CA was heated in a drum to 40° C. to 50° C. and mixed in case of an uneven distribution of its ingredients. After mixing until homogeneity, the other ingredients of group 1 (see table 2) were added. It was mixed again until homogeneity and then the temperature was increased to 85° C. to 90° C. At this temperature, the ingredients of Group 2 (see Table 2) were added and mixed in until homogeneous. This was then repeated with the ingredients of Group 3 (3a and 3b, see Table 2). The ingredients of Group 4 (see Table 2) were homogeneously mixed together and also added to the previously prepared mixture and mixed in until homogeneity was achieved. After that, the temperature was no longer actively maintained at 85° C. to 90° C., but it was only ensured that it did not drop to 70° C. or less. Finally, the mixture was kept at a temperature above 70° C. for filling or packaging. The resulting mixture was then poured into a pin/piece mould. The mixture was then allowed to cool and solidify.

The composition produced in the above-mentioned quantities is particularly suitable for formulating the conditioner as a multi-purpose form, especially in stick form.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A solid hair cosmetic composition comprising—based on the total weight of the cosmetic composition—
    a) from about 30.0 to about 60.0% by weight of at least one polyhydric alcohol,
    b) from about 0.1 to about 15.0% by weight of at least one cationic surfactant, wherein the at least one cationic surfactant comprises an alkylquat, an esterquats, a quaternary imidazoline, an amidoamine and/or a cationized amidoamine, or a combination thereof, and wherein the at least one cationic surfactant comprises a hydroxypropyltrimonium inulin,
c) from about 0.1 to about 20.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and
d) from about 0.1 to about 40.0% by weight of at least one polysaccharide.

2. The solid hair cosmetic composition according to claim 1, wherein the at least one cationic surfactant comprises a surfactant salt with the INCI designation cetrimonium and/or behentrimonium.

3. The solid hair cosmetic composition according to claim 1, comprising as component c)
cetyl alcohol, stearyl alcohol, or mixtures thereof.

4. The solid hair cosmetic composition according to claim 1, comprising as polysaccharide d) starch and/or modified starch and/or dextrins.

5. The solid hair cosmetic composition according to claim 1, wherein the at hydroxypropyltrimonium inulin has a cationic charge density of greater than about 3.5 meq/g.

6. A method for preparing a solid hair conditioning composition according to claim 1, comprising:
a) mixing the solid hair cosmetic composition according to claim 1 with sufficient heat and agitation to ensure that all ingredients are melted and/or evenly distributed to form a resulting mixture, and
b) allowing the resulting mixture to cool and solidify.

7. The solid hair cosmetic composition according to claim 1, wherein the at least one cationic surfactant further comprises a cationic polygalactomannan derivative, where the cationic polygalactomannan derivative has been modified with hydroxypropyltrimethylammonium groups.

8. A solid hair cosmetic composition, wherein the solid hair cosmetic composition consists of:
water;
citric acid;
cetrimonium chloride;
glycerine;
cetearyl alcohol;
palmitic acid and/or stearic acid;
glyceryl stearate;
maltodextrin;
hydroxypropyl starch phosphate;
corn starch;
butyrospermum parkii;
prunus armeniaca seed oil;
phenoxyethanol; and
perfume.

9. The solid hair cosmetic composition according to claim 8, wherein the solid hair cosmetic composition consists of:
the citric acid in an amount of 0.25 weight percent;
the cetrimonium chloride in an amount of 8 weight percent;
the glycerine in an amount of 35 weight percent;
the cetearyl alcohol in an amount of from 2 to 5 weight percent;
the palmitic acid and/or stearic acid in an amount of from 2 to 5 weight percent;
the glyceryl stearate in an amount of from 2.5 to 5 weight percent;
the maltodextrin in an amount of 1 weight percent;
the hydroxypropyl starch phosphate in an amount of 1.5 weight percent;
the corn starch in an amount of from 10 to 17.25 weight percent;
the butyrospermum parkii in an amount of 0.5 weight percent;
the prunus armeniaca seed oil in an amount of 2 weight percent; and
the phenoxyethanol in an amount of 1 weight percent.

10. The solid hair cosmetic composition according to claim 8, wherein the solid hair cosmetic composition comprises consists of:
the citric acid in an amount of 0.25 weight percent;
the cetrimonium chloride in an amount of 8 weight percent;
the glycerine in an amount of 35 weight percent;
the cetearyl alcohol in an amount of 5 weight percent;
the palmitic acid and/or stearic acid in an amount of 5 weight percent;
the glyceryl stearate in an amount of 5 weight percent;
the maltodextrin in an amount of 1 weight percent;
the hydroxypropyl starch phosphate in an amount of 1.5 weight percent;
the corn starch in an amount of 17.25 weight percent;
the butyrospermum parkii in an amount of 0.5 weight percent;
the prunus armeniaca seed oil in an amount of 2 weight percent; and
the phenoxyethanol in an amount of 1 weight percent.

11. The solid hair cosmetic composition according to claim 8, wherein the solid hair cosmetic composition comprises consists of:
the citric acid in an amount of 0.25 weight percent;
the cetrimonium chloride in an amount of 8 weight percent;
the glycerine in an amount of 35 weight percent;
the cetearyl alcohol in an amount of 2 weight percent;
the palmitic acid and/or stearic acid in an amount of 2 weight percent;
the glyceryl stearate in an amount of 2.5 weight percent;
the maltodextrin in an amount of 1 weight percent;
the hydroxypropyl starch phosphate in an amount of 1.5 weight percent;
the corn starch in an amount of 10 weight percent;
the butyrospermum parkii in an amount of 0.5 weight percent;
the prunus armeniaca seed oil in an amount of 2 weight percent; and
the phenoxyethanol in an amount of 1 weight percent.

* * * * *